(12) United States Patent
Kraft et al.

(10) Patent No.: US 9,427,519 B2
(45) Date of Patent: Aug. 30, 2016

(54) CARTRIDGE ADAPTER FOR USE IN AN INFUSION SYSTEM

(71) Applicant: Roche Diagnostics International AG, Rotkreuz (CH)

(72) Inventors: Torsten Kraft, Solothurn (CH); Hanspeter Stoller, Bern (CH); Simon Scheurer, Bern (CH); Christian Thalmann, Kehrsiten (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 18 days.

(21) Appl. No.: 14/473,202

(22) Filed: Aug. 29, 2014

(65) Prior Publication Data

US 2014/0378938 A1 Dec. 25, 2014

Related U.S. Application Data

(63) Continuation of application No. 12/750,177, filed on Mar. 30, 2010, now Pat. No. 8,876,770, which is a continuation of application No. PCT/EP2008/008256, filed on Sep. 29, 2008.

(60) Provisional application No. 60/976,500, filed on Oct. 1, 2007.

(51) Int. Cl.
| | |
|---|---|
| *A61M 1/00* | (2006.01) |
| *A61M 5/162* | (2006.01) |
| *A61M 5/142* | (2006.01) |
| *A61M 5/145* | (2006.01) |
| *A61M 5/172* | (2006.01) |
| *F16L 21/00* | (2006.01) |
| *A61M 5/24* | (2006.01) |

(52) U.S. Cl.
CPC .......... *A61M 5/162* (2013.01); *A61M 5/14244* (2013.01); *A61M 5/14566* (2013.01); *A61M 5/172* (2013.01); *F16L 21/00* (2013.01); *A61M 2005/14264* (2013.01); *A61M 2005/2418* (2013.01); *A61M 2202/07* (2013.01); *A61M 2205/121* (2013.01)

(58) Field of Classification Search
CPC ......... A61M 5/14566; A61M 5/1456; A61M 2005/14573; A61M 2005/2418
See application file for complete search history.

(56) References Cited

U.S. PATENT DOCUMENTS

| | | | |
|---|---|---|---|
| 5,360,410 A * | 11/1994 | Wacks | A61M 5/20 604/110 |
| 5,520,653 A | 5/1996 | Reilly et al. | |
| 5,776,116 A | 7/1998 | Lopez et al. | |
| 6,277,095 B1 | 8/2001 | Kriesel et al. | |
| 6,585,698 B1 * | 7/2003 | Packman | A61M 5/24 604/207 |

(Continued)

OTHER PUBLICATIONS

European Patent Office Search Report and Written Opinion mailed Feb. 2, 2009 in reference to European Patent Application No. PCT/EP2008/008256 filed Sep. 29, 2008.

*Primary Examiner* — Emily Schmidt
(74) *Attorney, Agent, or Firm* — Dinsmore & Shohl LLP

(57) ABSTRACT

Infusion systems for pumping fluid into a body of a user, and methods for providing infusion systems, are disclosed. The infusion systems include an infusion pump, wherein the infusion pump comprises an infusion pump housing including a cavity. A fluid storage is removably inserted into the cavity of the infusion pump housing wherein, the fluid storage comprises a cartridge and an adapter connected to the cartridge such that the adapter encases the cartridge, and an infusion set is removably connected to the fluid storage.

11 Claims, 5 Drawing Sheets

(56) References Cited

U.S. PATENT DOCUMENTS

| | | |
|---|---|---|
| 7,497,843 B1 | 3/2009 | Castillo et al. |
| 2003/0130618 A1 | 7/2003 | Gray et al. |
| 2007/0088271 A1* | 4/2007 | Richards ........... A61M 5/14244 604/151 |
| 2007/0167912 A1 | 7/2007 | Causey et al. |

* cited by examiner

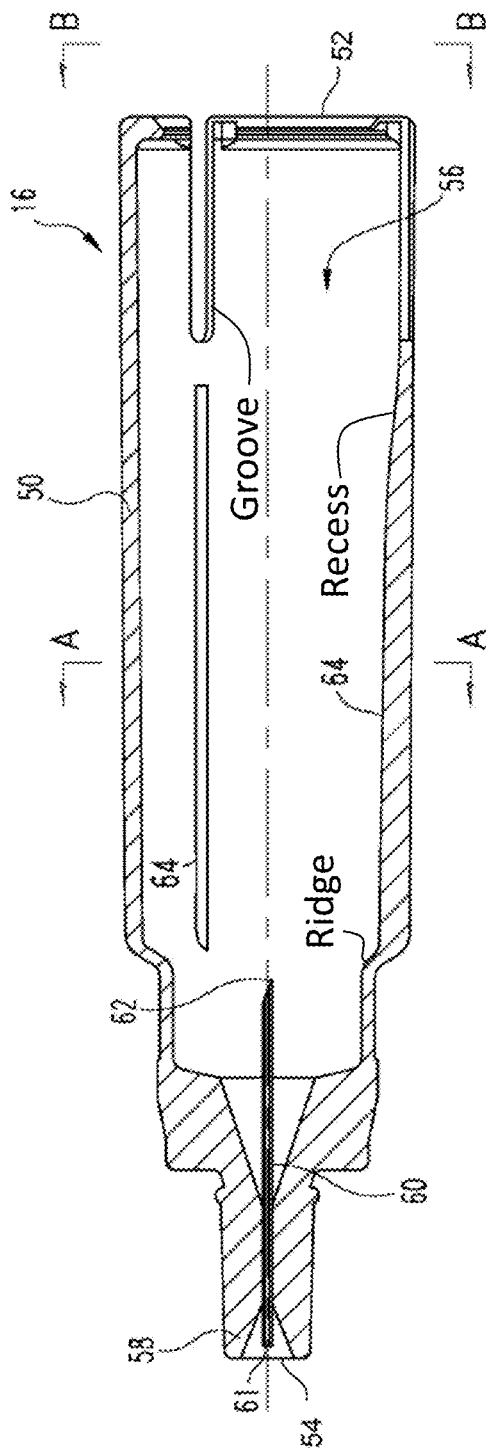
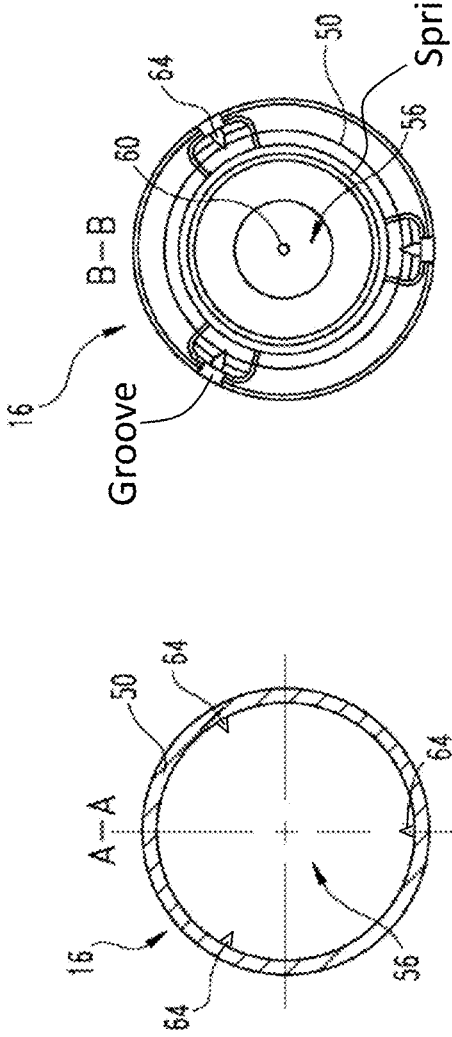
Fig. 4
Fig. 6
Fig. 5

CARTRIDGE ADAPTER FOR USE IN AN INFUSION SYSTEM

CROSS REFERENCE TO RELATED APPLICATIONS

This application is a continuation of U.S. application Ser. No. 12/750,177 filed Mar. 30, 2010, which is a continuation of International Application No. PCT/EP2008/008256 filed Sep. 29, 2008, which claims priority to U.S. Provisional Application No. 60/976,500 filed on Oct. 1, 2007.

TECHNICAL FIELD

The embodiments described herein relate to infusion pumps for dispensing medication. More specifically the embodiments relate to adapters that can be attached to fluid cartridges for dispensing medication from infusion pumps.

BACKGROUND

Medical devices that pump medication into an individual are known and commonly used in the medical industry. Typically the type of medication that is pumped from such medical devices depends on the medical condition that is to be treated. For example, it is getting increasingly common to deliver insulin using an insulin pump to treat a diabetic patient.

Typically, the medical pump devices use a reservoir or a cartridge that contains the medicine to be delivered. The overall size of the medical pump system depends on the size of the cartridge that needs to be used. Since manufacturing of a medical pump device is expensive, manufacturers typically decide which size cartridge they are going to use and design their medical pump systems based on such a size consideration. This limits the cartridges and treatments to sizes that are pre-determined by the manufacturer of the medical pump system.

Therefore, a need exists for alternative infusion systems offering additional flexibility in cartridge sizing.

SUMMARY

It is against the above background that embodiments of the present disclosure are described.

According to one embodiment, an infusion system for pumping fluid into a body of a user includes an infusion pump, wherein the infusion pump comprises an infusion pump housing including a cavity. A fluid storage is removably inserted into the cavity of the infusion pump housing wherein, the fluid storage comprises a cartridge and an adapter connected to the cartridge such that the adapter encases the cartridge, and an infusion set is removably connected to the fluid storage.

In another embodiment, an infusion system for pumping fluid into a body of a user includes: an infusion pump housing, a cavity disposed within the infusion pump housing, a cartridge, and an adapter comprising a connection and a cannula. Wherein, the adapter encases and is connected to the cartridge. The cannula is inside the cartridge. And, the adapter connects into the cavity.

In yet another embodiment, a method of providing an infusion system for pumping fluid into a body of a user, where the system includes an infusion pump housing with a cavity, includes: placing a cartridge into the cavity of the infusion pump housing; connecting an adapter comprising a connection and a cannula to the cartridge such that the adapter encases the cartridge; and inserting the cannula into the cartridge when the adapter is connected to the cartridge.

BRIEF DESCRIPTION OF THE DRAWINGS

The following detailed description of the embodiments of the present invention can be best understood when read in conjunction with the following drawings, where like structure is indicated with like reference numerals and in which:

FIG. 4 depicts a perspective view of the adapter according to one or more of the embodiments shown and described herein;

FIG. 5 depicts a cross-sectional view of the adapter along line A-A of FIG. 4 according to one or more of the embodiments shown and described herein;

FIG. 6 depicts an end view of the adapter along line B of FIG. 4 according to one or more of the embodiments shown and described herein.

Figure 1:
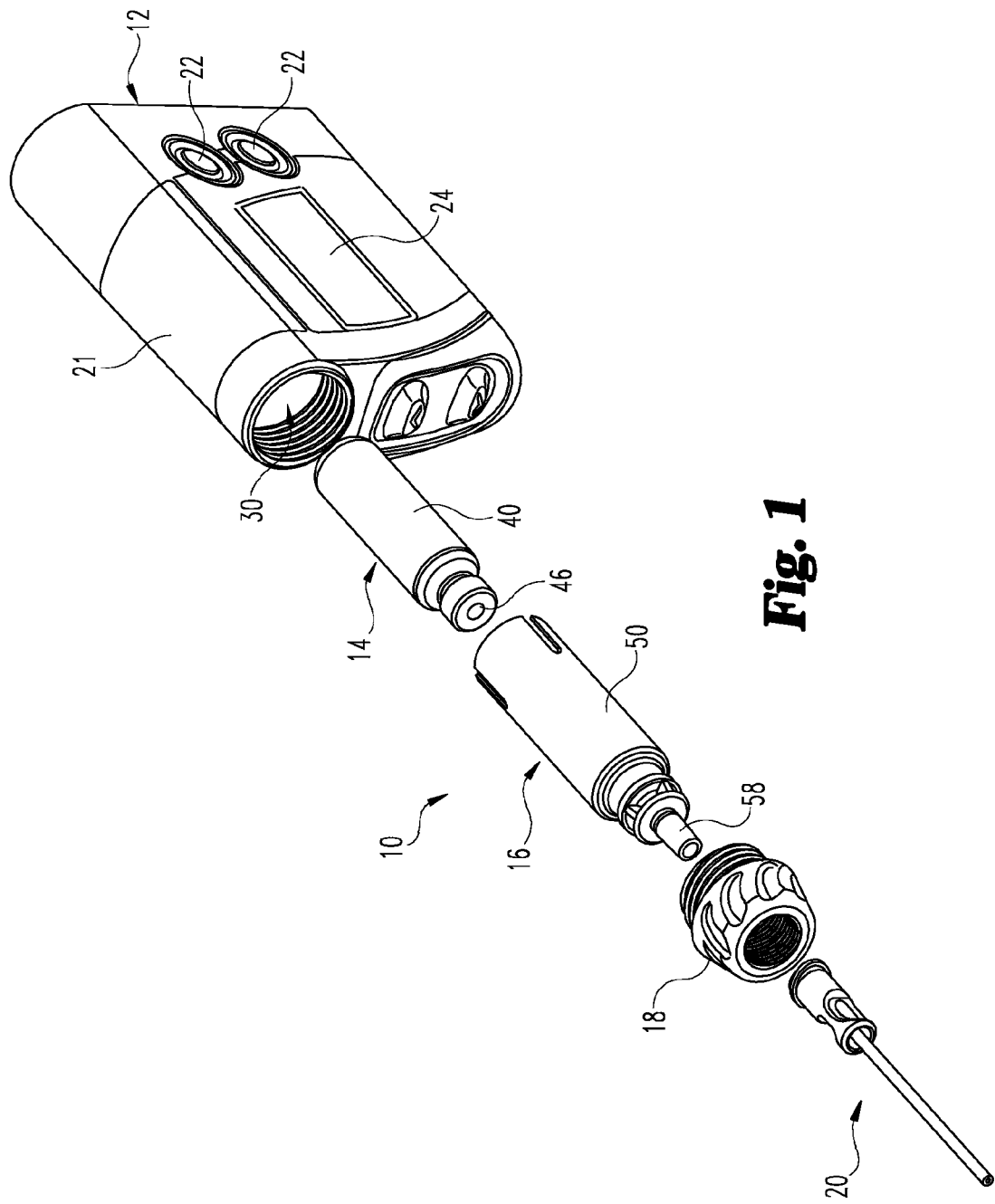
FIG. 1 depicts an exploded view of the infusion delivery system according to one or more of the embodiments shown and described herein.

The drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

In accordance with one embodiment, the present invention comprises an infusion system for pumping fluid into a body of a user. The infusion system has an a infusion pump with an infusion pump housing including a cavity. The cavity is designed to receive a fluid storage, such that the a fluid storage can be removably inserted into the infusion pump housing. The fluid storage comprises a cartridge and an adapter, such that the adapter removably encases the cartridge. Additionally, the infusion system comprises a cap that is attached to the infusion pump housing holding the fluid storage in place inside the infusion pump housing.

According to an embodiment of the present disclosure, the adapter comprises a hollow interior such that the cartridge can be snapped into the hollow interior. The adapter may also comprise a cannula that pierces the septum of the cartridge when the adapter encases the cartridge. The adapter is designed such that it can receive differently sized cartridges while fitting into the infusion pump. Additionally, it is noted that the adapter may comprise a needle instead of a cannula.

In another embodiment, the adapter comprises a connection connected to an infusion set. The connection may be the industry standard "Luer" connection or any other proprietary connection for use with infusion sets.

Another embodiment of the present disclosure comprises an infusion system for pumping fluid into a body of a user. The infusion system has an infusion pump with an infusion pump housing including a cavity. A fluid storage is removably inserted into the cavity. The fluid storage comprises a cartridge and an adapter, such that the adapter removably encases the cartridge. Additionally, the infusion system comprises a cap that is attached to the infusion pump housing holding the fluid storage in place inside the infusion pump housing.

In an embodiment of the present disclosure, the adapter comprises an adapter housing that is formed of two parts. The first part of the adapter housing is placed into the cavity of the infusion pump. The first part of the adapter housing may be removably or fixedly attached into the cavity. The second part comprises the cannula and the connection, and is coupled to the first part after the cartridge is inserted into the adapter.

In another embodiment of the present invention, the adapter is designed such that it is possible to use a kind of pen cartridge which has a code cap.

In yet another embodiment, the adapter is designed such that it works as a spring or a shock absorbing element to cover the tolerances between the cartridge and the infusion pump housing. For example, the hollow interior of the adapter may be provided with a spring mechanism or any shock absorbing material.

In an embodiment of the present disclosure, the adapter is formed of a first part and a second part. The first part is attached to the infusion pump housing and comprises a shock absorbing element.

In another embodiment, the adapter comprises a valve between the cannula and the connection to prevent the free flow of the medication from the cartridge into the infusion set when the plunger is not connected to the drive system.

In a further embodiment, the adapter comprises a mechanism to transfer torque from the adapter onto the cartridge. For example, such a mechanism could include a plurality of ribs provided in the interior of the adapter housing.

These and other features and advantages of the present disclosure will be more fully understood from the following detailed description taken together with the accompanying claims. It is noted that the scope of the claims are defined by the recitations therein and not by the specific discussion of the features and advantages set forth in the present description.

Furthermore, the following description of embodiments of the present disclosure is merely exemplary in nature and not intended to limit the disclosure.

Figure 3:
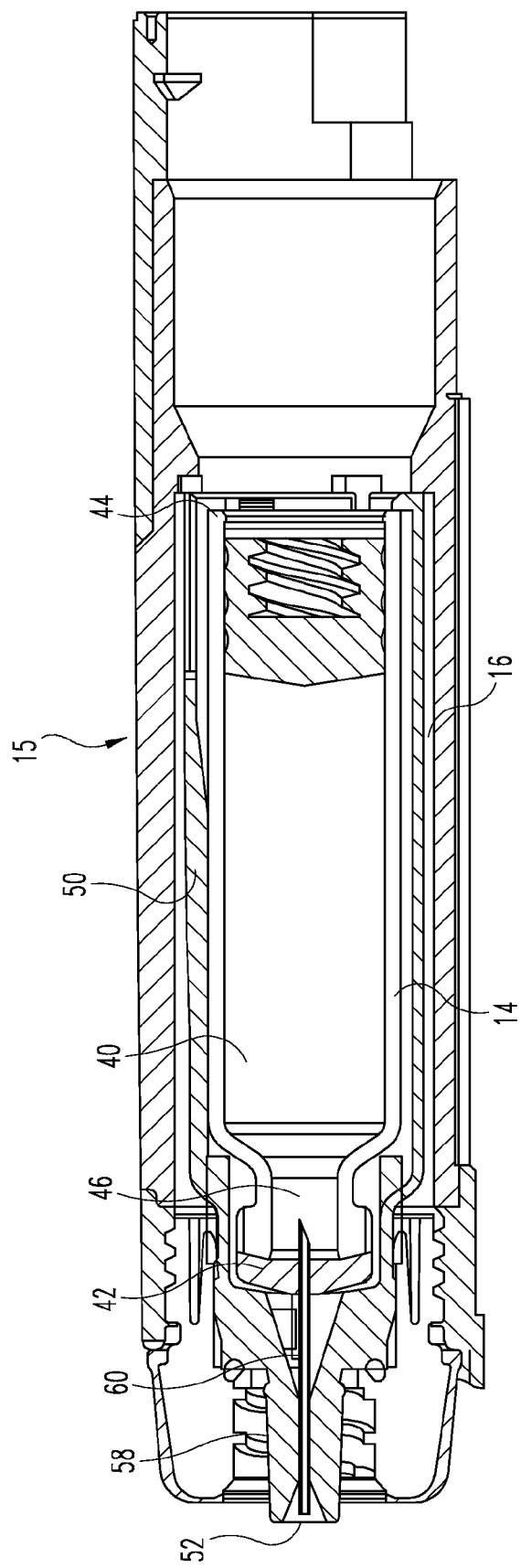
FIG. 3 depicts a perspective view of the cartridge and the adapter according to one or more of the embodiments shown and described herein.

An embodiment of the present disclosure is depicted in FIGS. 1 and 3. An infusion system 10 comprises an infusion pump 12, a fluid storage 15, a cap 18 to hold the fluid storage 15 in place and an infusion set 20 (not completely shown) that is connected to a cartridge 14 through the cap 18. The infusion pump 12 is depicted in the drawings as an insulin pump such as the insulin pump sold by Disetronic Medical System under the name ACCU-CHEK SPIRIT®. Although an insulin pump is depicted, it should be understood that this disclosure is not limited to insulin pumps, and any pump can be used to deliver medication.

Referring still to FIGS. 1 and 3, embodiments of the infusion pump 12 comprise an infusion pump housing 21 that has at least one control 22 to control the infusion of medication from fluid storage 15. The infusion pump 12 also includes a display 24 to display information relevant to the operation of the infusion pump 12. Although not shown in the drawings, the infusion pump 12 may have additional controls or buttons to effectively operate the infusion pump 12. Additionally, the infusion pump 12 may be controlled remotely to dispense medication using a remote control device such as a smart phone, a PDA or any other mobile device. Furthermore, the infusion pump 12 may be a one time use pump such that after the dispensing of the medication the pump is disposed.

Figure 2:
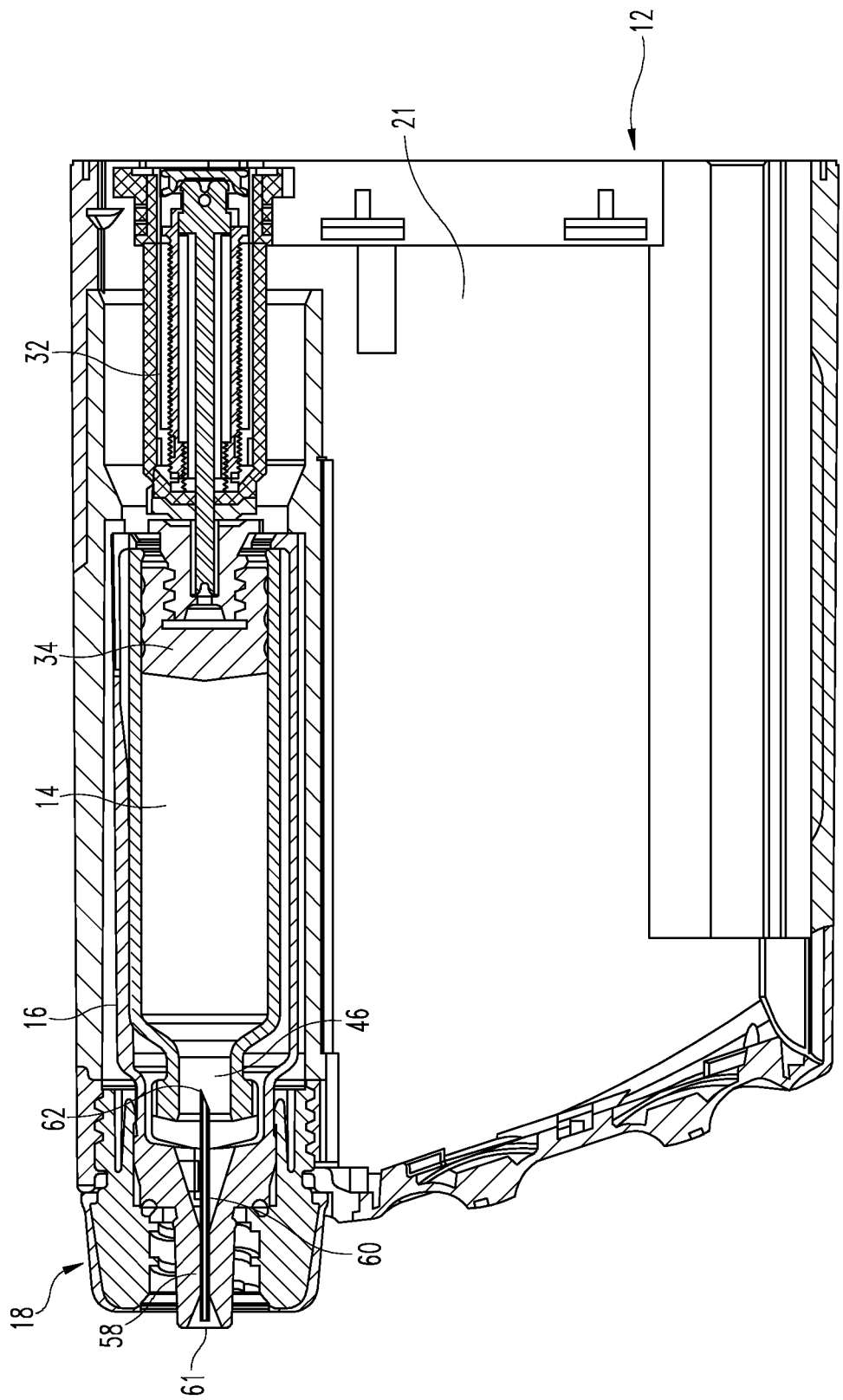
FIG. 2 depicts a perspective view of the cartridge and the adapter according to one or more of the embodiments shown and described herein.

Referring now to FIGS. 1, 2 and 3, in an embodiment of the present disclosure the fluid storage 15 comprises a cartridge 14 and an adapter 16, and the infusion pump 12 comprises an infusion pump housing 21. The infusion pump housing 21 has a cavity 30 for receiving the fluid storage 15. In one embodiment, the fluid storage 15 can be removably inserted into the cavity such that after the medication is consumed, a new fluid storage 15 can be inserted into the cavity 30. The fluid storage 15 is inserted into the cavity 30, and cooperates with a drive system 32 that advances a plunger 34 in order to dispense medication there from. In operation, when the infusion pump 12 is given the required commands/instructions, the drive system 32 moves the plunger 34 such that the medication is dispensed from the cartridge 14 through the infusion set 20.

In another embodiment, depicted in FIGS. 1 and 2, the cartridge 14 contains a medication (not shown) that can be dispensed. For example, if the infusion pump 12 is an insulin pump, then the cartridge 14 contains insulin. The medication may be pre-filled into the cartridge 14 such that when the medication is consumed, the cartridge 14 is disposed of. An example of a pre-filled cartridge is sold by Novo Nordisk A/S under the name NOVOLOG®. Alternatively, the cartridge 14 may be refilled with medication as needed from a vial provided by the manufacturer of the medication. An embodiment of the cartridge 14 contains a cartridge housing 40 having a first side 42 and a second side 44. Depending on the medication and its expected shelf life, the cartridge housing 40 can be made of plastic, glass or any other suitable material. In another embodiment, the cartridge 14 is inserted into the cavity 30, and the second side 44 cooperates with the drive system 32 of the infusion pump 12. The first side 42 of the cartridge 14 comprises a septum 46, which is sealable, and a hollow needle from the adapter 16 is removably inserted into the septum 46 (as will be explained in detail herein). Alternatively, in another embodiment, the cartridge 14 and the adapter 16 are coupled together. The coupled cartridge 14 and adapter 16 are then inserted as a unit into the cavity 30 of the infusion pump 12. The second side 44 of the cartridge 14 couples with the drive system 32 such that medication from the cartridge 14 can be infused in a controlled manner.

Referring now to FIGS. 2, 3 and 4, an embodiment of the adapter 16 comprises an adapter housing 50 having a first end 52 and a second end 54. The adapter housing 50 has a hollow interior 56 such that the cartridge 14 can be removably received in the hollow interior 56. In such an arrangement, the adapter 16 encases the cartridge 14. The shape of the adapter housing 50 is such that the adapter 16 can easily fit into the cavity 30 of the infusion pump 12. In addition, the shape of the adapter housing 50 is compatible with the outer shape of the cartridge housing 40. The first end 52 of the adapter 16 is open and the cartridge 14 is inserted into the adapter 16 through the first end 52. In one embodiment, the cartridge 14 is first inserted into the infusion pump 12. The adapter 16 then slides over the cartridge 14, and engages with and covers the cartridge 14. In another embodiment, the cartridge 14 and the adapter 16 are inserted as a unit into the infusion pump 12. The cartridge 14 slides into the hollow interior 56 of the adapter 16 thereby forming the fluid storage 15. The fluid storage 15 is then inserted into the cavity 30 of the infusion pump housing 21.

Referring to FIGS. 1, 2, 3, and 4, in embodiments of the infusion system 10, the second end 54 of the adapter housing 50 comprises a connection 58 connecting the fluid storage 15 to the infusion set 20. The connection 58 can be a standard "Luer" connection or any proprietary connection suitable for connecting the infusion set 20 to the infusion pump 12. The second end 54 of the adapter 16 also includes a cannula 60. The cannula 60 at a distal end 61 is fixedly connected to the interior of the adapter housing 50. The cannula 60 comprises a sharp tip 62 that extends inside the adapter housing 50. When the cartridge 14 is inserted inside the adapter 16 or when the adapter 16 slides over the cartridge 14, the cannula 60 pierces the septum 46 of the cartridge 14, and comes into contact with medication inside the cartridge 14. The cannula 60 is hollow such that medication can flow into the infusion set 20. Additionally, the cannula 60 can be formed from plastic or other materials such as steel.

In another embodiment, depicted in FIGS. 4, 5 and 6, the adapter 16 has an attachment holding the cartridge 14 in place. The attachment may be provided at the first end 52 or the second end 54 of the adapter housing 50. Further, the attachment can be provided in the interior of the adapter housing 50 or can be provided at any other suitable place. In another embodiment, in order to ensure that the adapter 16 can receive different cartridge sizes into the hollow interior 56, the adapter housing 50 comprises a spring mechanism, such that the cartridge 14 is snapped into the adapter 16. The attachment can attach or snap fit the adapter 16, and may include groves, ridges, recess or any other mechanism that will hold a tight fit between the adapter 16 and the cartridge 14.

In one embodiment, the adapter 16 and the cartridge 14 are connected with each other, and cannot be separated for reuse. In other words once the medication is consumed from the cartridge 14, the adapter 16 and the cartridge 14 are removed as a unit from the infusion pump 12 and disposed as a unit. In another embodiment, the adapter 16 and the cartridge 14 are separable.

Figure 7:
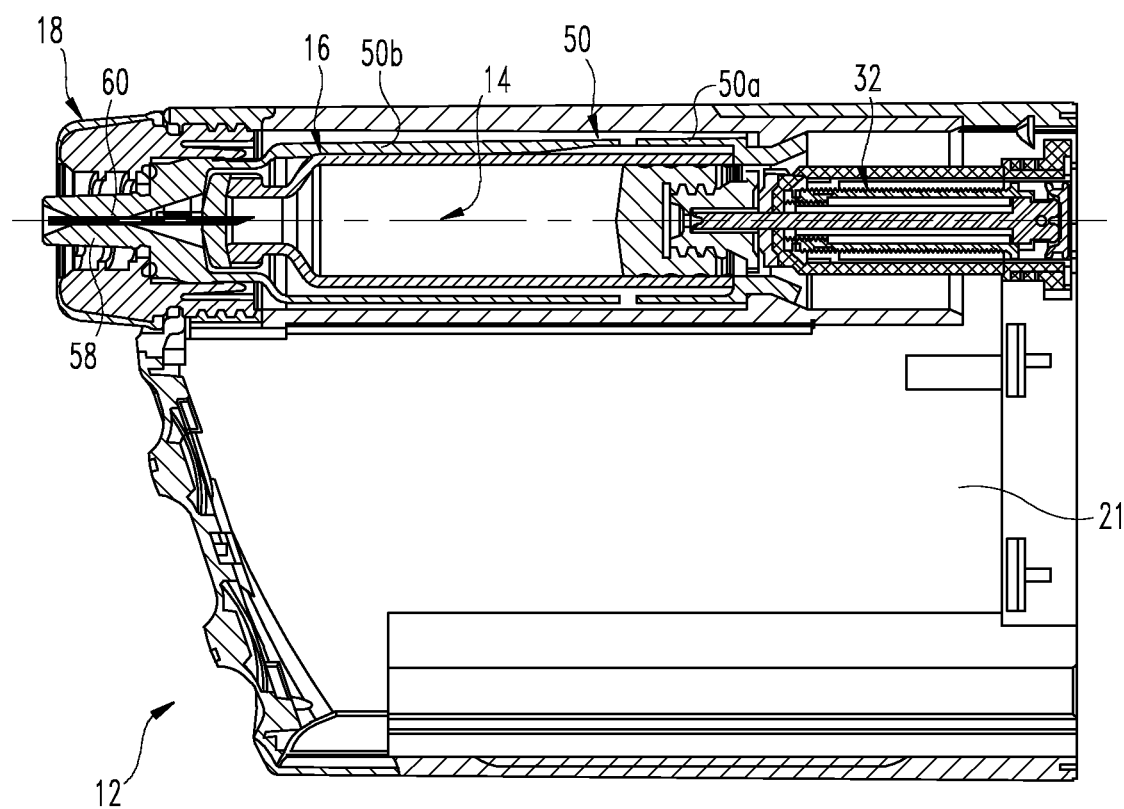
FIG. 7 depicts a perspective view of the cartridge and the two part adapter housing according to one or more of the embodiments shown and described herein.

In another embodiment, as depicted in FIG. 7, the adapter 16 comprises an adapter housing 50 that is formed of a first part 50a and a second part 50b. The first part 50a of the housing is placed into the cavity 30 of the infusion pump 12. The first part 50a of the adapter housing 50 may be removably or fixedly attached into the cavity 30 and around the plunger of the infusion pump. The second part 50b, comprising the cannula 60 and the connection 58, is coupled or mated to the first part 50a of the adapter housing 50 after the cartridge 14 is inserted into the adapter 16. Additionally, the second part 50b can be coupled to the first part 50a by different methods such as placing the second part 50b on top of the first part 50a, or by snapping or fastening the first part 50a and the second part 50b together.

Referring still to FIG. 7, another embodiment of the adapter housing 50 is formed of a first part 50a and a second part 50b. Functionalities are transferred from the adapter housing 50 to the first part 50a that is attached within the infusion pump housing 21. For example, the first part 50a may be provided with a spring or a shock absorbing material to cover the tolerances between the adapter and the pump housing. Furthermore, the first part 50a may be coded or provided with a coding mechanism such that it detects correct attachment of the cartridge 14 and/or the adapter 16 into the infusion pump housing 21.

In another embodiment of the present disclosure the adapter 16 uses a pen cartridge which has a code cap.

In yet another embodiment, depicted in FIGS. 4 and 7, the adapter 16 works as a spring or a shock absorbing element to cover the tolerances between the cartridge 14 and the infusion pump housing 21. For example, in FIG. 4 the hollow interior 56 of the adapter 16 may be provided with a spring mechanism or any shock absorbing material.

In a further embodiment (FIG. 2), the adapter 16 comprises a valve between the cannula 60 and the connection 58 to prevent free flow of the medication into the infusion set when the plunger 34 is not connected to the drive mechanism.

Referring now to FIGS. 5 and 6, another embodiment of the adapter 16 comprises a mechanism to transfer torque from the adapter 16 onto the cartridge 14. For example, such mechanism could include a plurality of ribs 64 provided in the hollow interior 56 of the adapter housing 50.

In the embodiments depicted in FIGS. 1, 2, 3 and 7, the cap 18 is coupled to the infusion pump housing 21 after the fluid storage 15 is inserted into the cavity 30. The cap 18 retains the cartridge 14 in the infusion pump 12. In one embodiment, the cap 18 locks the cartridge 14 in the infusion pump housing 21. In another embodiment, the cap 18 ceases or prevents the dispensation of medication if the cap 18 is not properly engaged with the infusion pump 12. In a further embodiment, the cap 18 water proofs the infusion pump 12. In yet another embodiment, the cap locks the fluid storage 15 of an infusion pump 12 to limit a disposable pump to a single use.

Referring still to FIGS. 1, 2, 3, and 7, embodiments of the infusion system 10 are operated by inserting the fluid storage 15 into the cavity 30 such that the cannula 60 integrated with the adapter 16 pierces the septum 46 of the cartridge 14 to create a fluidic path. The cap 18 is then coupled to the infusion pump housing 21 such that the fluid storage 15 is held in place inside the cavity 30, thereby engaging the drive system 32. The connection 58 on the adapter 16 is then connected to the infusion set 20. The user then initiates commands/instructions either using the at least one control 22 on the infusion pump 12 or a remote device (not shown) to pump the medication from the cartridge 14 into the body of the user.

It is noted that terms like "preferably", "commonly", and "typically" are not utilized herein to limit the scope of the disclosure or to imply that certain features are critical, essential, or even important to the structure or function of the claimed invention. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the disclosure in detail and by reference to specific embodiments thereof, it will be apparent that modification and variations are possible without departing from the scope of the present disclosure defined in the appended claims. More specifically, although some aspects of the present disclosure are identified herein as preferred or particularly advantageous, it is contemplated that the present disclosure is not necessarily limited to these preferred aspects of the disclosure.

What is claimed is:

1. A monolithic adapter for receiving cartridges of differing sizes for pumping fluid into a body, the monolithic adapter comprising:
    a monolithic adapter housing comprising a first end and a second end, the adapter housing
    comprising a hollow interior such that at least one of the cartridges can be removably received in the hollow interior through the first end of the adapter housing and fully encased within the adapter housing; and
    a cannula that pierces a septum of the at least one of the cartridges when the adapter encases the at least one of the cartridges;
    wherein the adapter housing comprises a spring or a shock absorbing material within the hollow interior of the adapter housing such that when the at least one of the cartridges is moved into the adapter housing toward the second end of the adapter housing, the at least one of the cartridges snaps into the adapter housing, the monolithic adapter being configured to receive the cartridges of differing sizes such that each snap fits within the adapter housing.

2. The method of claim 1 wherein the monolithic adapter comprises the shock absorbing material within the hollow interior of the monolithic adapter housing.

3. The monolithic adapter of claim 1 wherein the adapter housing comprises at least one of grooves, ridges, and recesses for the snap fit of the at least one of the cartridges.

4. The monolithic adapter of claim 1 wherein the at least one of the cartridges is coupled to the first end and the second end of the adapter housing.

5. The monolithic adapter of claim 1 wherein the adapter housing comprises a cylindrical shape, and the shape of the adapter housing is compatible with the outer shape of a housing of the at least one of the cartridges.

6. The monolithic adapter of claim 1 wherein the monolithic adapter comprises the shock absorbing material disposed within the hollow interior and the shock absorbing material disposed between the monolithic adapter and an infusion pump housing to which the monolithic adapter is couplable.

7. The monolithic adapter of claim 1 further comprising a torque transfer mechanism that transfers torque from the adapter to the at least one of the cartridges, the torque transfer mechanism comprising a plurality of ribs equally spaced in the hollow interior of the in the adapter housing.

8. The monolithic adapter of claim 7 wherein the plurality of ribs comprises three ribs.

9. The monolithic adapter of claim 1 wherein the adapter housing comprises two longitudinal slits extending from the first end toward the second end.

10. The monolithic adapter of claim 1 wherein the monolithic adapter comprises the spring within the hollow interior of the monolithic adapter housing.

11. The monolithic adapter of claim 1 wherein the cartridge is a pen cartridge.

* * * * *